United States Patent [19]

Novack et al.

[11] Patent Number: 4,664,886

[45] Date of Patent: May 12, 1987

[54] TRIMODE GAS DETECTION INSTRUMENT

[75] Inventors: Robert L. Novack, Evans City; John M. Fruhwald, Pittsburgh, both of Pa.

[73] Assignee: Bacharach, Inc., Pittsburgh, Pa.

[21] Appl. No.: 560,785

[22] Filed: Dec. 13, 1983

[51] Int. Cl.[4] .............................................. G01N 27/00
[52] U.S. Cl. ......................................... 422/94; 73/23; 204/406; 422/98; 436/136
[58] Field of Search ................. 422/94, 98; 73/23; 436/137; 204/406, 427; 123/489

[56] References Cited

U.S. PATENT DOCUMENTS

| | | | |
|---|---|---|---|
| 3,364,476 | 1/1968 | Kahn | 340/213 |
| 3,558,280 | 1/1971 | Panson et al. | 23/254 |
| 3,943,775 | 3/1976 | De Baun | 73/432 |
| 4,069,018 | 1/1978 | Karna et al. | 23/232 |
| 4,101,277 | 7/1978 | Hickam | 23/232 |
| 4,109,509 | 8/1978 | Cramer et al. | 73/23 |
| 4,128,458 | 12/1978 | Obiaya | 204/1 |
| 4,134,289 | 1/1979 | Bohl et al. | 73/23 |
| 4,173,886 | 11/1979 | Archbold et al. | 73/23 |
| 4,283,256 | 8/1981 | Howart et al. | 436/137 X |
| 4,388,822 | 6/1983 | Heller | 73/23 |

OTHER PUBLICATIONS

Miller et al.; Oxygen Deficiency Hazards Associated with Liquified Gas Systems: Derivation of a Program of Controls; NTIS Report No. FNAL-TN-1163 Jan. 1983.

*Primary Examiner*—Barry S. Richman
*Assistant Examiner*—Michael S. Gzybowski
*Attorney, Agent, or Firm*—Webb, Burden, Robinson & Webb

[57] ABSTRACT

A trimode gas detection instrument having three operating modes, one which monitors the level of combustible gases, a second which monitors oxygen, and a third which monitors the displacement of air by an unknown gas. Only two sensors are used, a combustible gas sensor and an oxygen sensor. A switch selects the input to a readout so that the user can quickly observe the concentration readings in any of the three modes. In the depletion mode the readout is calibrated in relation to the inverse of the normal concentration of oxygen in air—i.e., zero depletion corresponds to an oxygen concentration of 21%. In the event that an unknown gas displaces air in a sample atmosphere, concentration of the unknown gas appears on the readout, such that zero oxygen corresponds to a concentration of 100% unknown gas.

8 Claims, 1 Drawing Figure

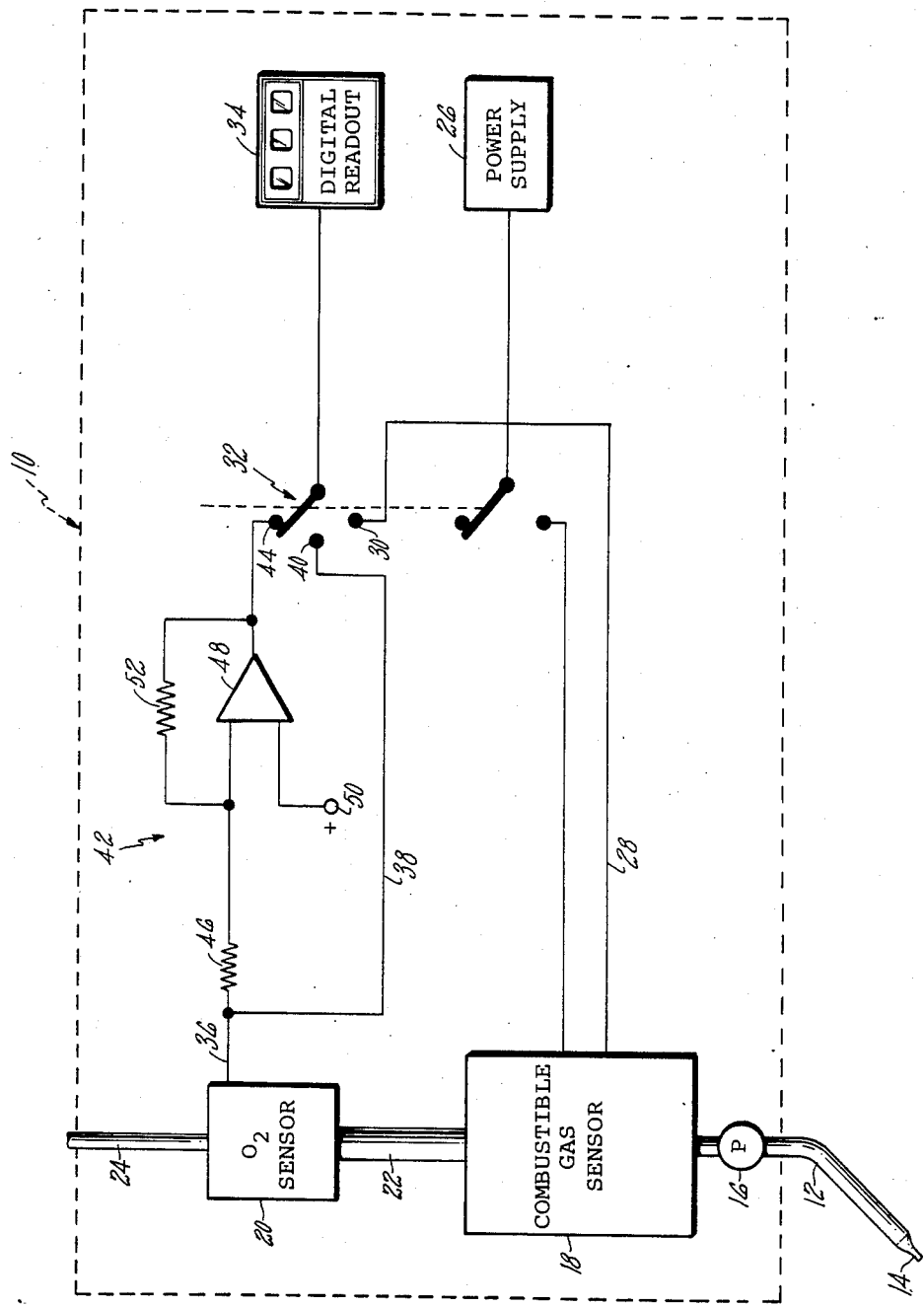

TRIMODE GAS DETECTION INSTRUMENT

DESCRIPTION

1. Technical Field

This invention relates to an apparatus for monitoring gaseous atmospheres, and more particularly, to a trimode gas detection instrument for monitoring various gas concentrations in a sampled atmosphere.

2. Background Art

Gas concentration levels in a confined atmosphere are of particular concern, primarily because of the danger to human life. As is well known, there are two general limits of concentration levels for combustible gases between which a flame will propagate or burn. These limits are known as the upper explosive limit (UEL) and the lower explosive limit (LEL). The LEL is the lowest concentration of a combustible gas that will ignite when exposed to an open flame or spark. The concentrations between the LEL and UEL is often referred to as the combustible range.

It will be appreciated that the combustible range of gas concentrations is not the only range of gas concentration which pose a hazard. Combustible gases, inert gases and other gases also pose a hazard because such gases displace the oxygen in air. Accordingly, if there is a sufficiently high concentration of a foreign gas such that the normal 20.9% oxygen concentration in the atmosphere is lowered, the loss of breathing oxygen poses a significant danger to human life.

Numerous different gas sensors have been proposed for measuring the concentration of inert gases and hydrocarbon-based gases in air. One prior art oxygen sensor is described in U.S. Pat. No. 3,558,280 issued Jan. 26, 1971 to A. J. Panson et al for "Solid State Oxygen Gauge". The disclosure in this patent describes a solid state oxygen sensitive element formed from a mixed valence oxide compound that exhibits a change in electrical resistance as a function of the change in the oxygen partial pressure of a sample gas. Also of interest is U.S. Pat. No. 4,109,509 issued Aug. 29, 1978 to R. L. Cramer et al for "Oxygen Monitor and Warning Device for an Aircraft Breathing System". A sensor responsive to the partial pressure of oxygen is connected to a chamber through which a sample of a breathable fluid is passed. The sensor produces an operational signal which is proportional to the concentration of oxygen in the breathable fluid.

Another well known gas sensor is the "catalytic" type in which a catalytic metal wire is heated by an electric current and exposed to a sample containing a combustible gas. As the combustible gas contacts the heated catalytic wire and burns, the generated heat changes the conductivity or the resistivity of the metal wire. A "Wheatstone bridge", or similar device, uses the change in resistance of an element as a measure of the concentration of the combustible gas in the sample.

Still other gas monitoring devices which are capable of identifying more than one gas in the atmosphere are also known. Of interest is U.S. Pat. No. 4,069,018 issued Jan. 17, 1978 to J. Karna for "Explosive Gas Monitoring Method and Apparatus". The apparatus described in this patent has a first channel for monitoring the concentration of combustible organic vapors in the atmosphere, and a second channel for determining the concentration of carbon monoxide. The apparatus can be augmented with an optional oxygen analyzer to measure the oxygen content in the atmosphere. Also of interest for its teaching of two gas detectors in a single apparatus is U.S. Pat. No. 4,134,289 issued Jan. 16, 1979 to T. Bohl for "Gas Sampling System Having a Flow Indicator". The gas sampling system described in this patent includes a combustible gas detector and an oxygen detector, both of which sample from a common inlet. Another device which includes a combustible gas sensor and an oxygen sensor is described in U.S. Pat. No. 3,943,775 issued Mar. 16, 1976 to B. DeBaun for "Method and Apparatus for Predicting the Explosiveness of a Volume Containing Inert Gas and Hydrocarbon Vapors When Mixed With Air". The oxygen analyzer utilizes a voltaic reaction in a solid electrolyte to correlate the oxygen concentration to the voltage produced by the voltaic reaction. The combustible gas analyzer induces an exothermic reaction in the region of a thermal pile to produce a voltage difference related to the concentration of the combustible gas.

DISCLOSURE OF INVENTION

It is an object of the present invention to provide a trimode gas detection instrument which is capable of monitoring oxygen levels, combustible gas levels and an unknown gas displacing the air.

An advantage of the trimode gas detection instrument according to the present invention is that a single catalytic oxygen sensor is used in two modes—first to measure the concentration of oxygen, and second to measure the displacement of air in the sample by an unknown gas.

A trimode gas detection instrument according to the present invention has multiple modes, one for monitoring oxygen concentrations, a second mode for monitoring displaced air and a third mode for monitoring combustible gases in the combustible range. The instrument includes a sampling means, a combustible gas sensor and an oxygen sensor, the oxygen sensor operating in two separate modes. A three-position switch allows the digital readout to be connected to either the combustible gas sensor signal, the oxygen sensor signal or the inverse of the oxygen sensor signal. In this latter mode, the readout is for the range of oxygen concentrations between that normal for air, and zero concentration of oxygen, thus indicating that all of the air in the sample has been displaced by unknown gas. The readout will show 0% unknown gas when displaying the inverse of the oxygen concentration in air and 100% when the unknown gas displaces all the air.

The foregoing and other objects, features and advantages of the present invention will become more apparent from the following description of preferred embodiments and the accompanying drawing.

BRIEF DESCRIPTION OF DRAWING

The drawing is a schematic illustration of the trimode gas detection instrument according to the present invention.

BEST MODE FOR CARRYING OUT THE INVENTION

Referring to the drawing, there is seen one embodiment of the trimode gas detection instrument according to the present invention, this embodiment operating in three distinct modes for gas monitoring. The trimode gas detection instrument is generally indicated by the numeral 10 and in preferred form is typically a portable gas monitoring instrument designed to provide a visual or audible reading indicating the concentration level of particular gases in the atmosphere. The instrument 10 may include a hand-held probe 12 which has sampling port 14 located at its tip. A passageway within the probe 12 leads from the sampling port 14 to a pump 16 which allows atmospheric samples to be continuously drawn into the gas detection instrument 10.

A combustible gas sensor 18 and an oxygen sensor 20 are provided and may be connected in series by a tube 22 to the pump 16 so the sampled atmosphere sequentially is presented to each sensor. An outlet tube 24 exhausts the sample back into the atmosphere.

A mode switch 32, such as a single throw, three-position switch, is provided for selecting either a combustible gas mode, oxygen sense mode, or air depletion mode, and may have two sections. One section selects the output signal to be directed to the readout, while the other section (the lower section in the drawing) disconnects the power supply 26 from the combustible gas sensor 18 when not in use to prevent overheating.

The combustible gas sensor 18 can be of the conventional catalytic type such as used in the Sniffer® 301 manufactured by Bacharach Instrument Company, which utilizes a platinum bead element. The combustible gas sensor 18 presents a combustible output signal on the line 28 which is proportional to the percentage of the LEL of the combustible gas in the sample.

The oxygen sensor 20 preferably is of the electrochemical type and provides an oxygen output signal on the line 36 which is proportional to the amount of oxygen in the sample presented to the oxygen sensor 20. As is known, the normal composition of air is approximately 78% $N_2$, 21% $O_2$, with about 1% of argon and other gases. Accordingly, if this ratio of oxygen in the sample decreases it is an indication that the air being sampled is becoming oxygen deficient.

A particular feature of the trimode gas detection instrument according to the present invention is that the oxygen output signal from the oxygen sensor 20 can be used in either one of two distinct modes. In one mode the signal is presented in an unmodified form through the line 38 to a terminal 40 of the mode switch 32. In its other mode of operation it is presented through an inverting circuit 42 to a terminal 44 of the mode switch 32. The inverting circuit 42 may consist of any one of a number of wellknown inverting circuits, one embodiment of which is depicted in the drawing. This embodiment includes an input resistor 46 connected to the line 36 to receive the output oxygen signal level from the sensor 20 and presents it to one terminal of an operational amplifier 48. The other terminal of the operational amplifier connects to a terminal 50 and a source of bias potential (not shown). A resistor 52 is coupled across the operational amplifier and feeds back a portion of the output signal to the input of the operational amplifier 48. The output is also connected to the terminal 44 of the mode switch 32.

In operation, the trimode gas detection instrument according to the present invention allows the user the option of selecting any one of its three modes of operation so that decisions about gas concentration in the atmosphere can be quickly made. For example, if the user of the trimode gas detection instrument is concerned about locating the source of a combustible gas, the first indication of such a leak would be a reading in the combustible gas mode. Full scale deflection, or 100% LEL is still a relatively low overall concentration of gas and 100% LEL would most likely be indicated prior to identifying the source of combustible gas. At this point, the trimode gas detection instrument could be switched to its displacement mode in which the digital readout 34 would then be displaying an indication of the amount of air displaced by the unknown gas. Accordingly, an increase in the reading of the digital readout 34 in the displacement mode would indicate that the user is approaching the source of the unknown gas.

It should be understood that various changes may be made to the trimode gas detection instrument according to the present invention. For example, a dual mode embodiment employing a single oxygen sensor could be made and would allow the user the option of observing the concentration of oxygen in one mode and in the second mode the amount of air which has been displaced by a concentration of an unknown gas.

Although this invention has been shown and described with respect to a preferred embodiment, it will be understood by those skilled in this art that various changes in form and detail thereof may be made without departing from the spirit and scope of the claimed invention.

We claim:

1. A gas monitoring apparatus having multiple modes of operation for monitoring concentration levels of combustible gases, oxygen and the amount of air displaced by an unknown gas in an atmosphere, comprising:
   sampling means for obtaining a sample of an atmospheric gaseous mixture;
   combustible gas sensing means connected to said sampling means for generating a combustible output signal proportional to the lower explosive limit of combustible gas in the sample;
   oxygen sensing means connected to said sampling means for generating an oxygen output signal proportional to the level of oxygen in the sample;
   air displacement sensing means connected to said oxygen sensing means for receiving said oxygen output signal and for therefrom generating a concentration of an unknown gas in the sample; and
   indicator means selectively connectable to any one of said combustible gas sensing means, said oxygen sensing means, or said displacement sensing means for providing a visual readout of the output signals.

2. A gas monitoring apparatus according to claim 1, wherein said oxygen sensing means comprises an electro-chemical oxygen sensor.

3. A gas monitoring apparatus according to claim 1, wherein said gas monitoring apparatus includes a mode switch, means for selecting between three distinct modes of operation wherein said mode switch means may alternatively connect one of said combustible gas sensing means, said oxygen sensing means or said air displacement sensing means to said indicator means.

4. A gas monitoring apparatus according to claim 3, wherein said indicator means comprises a digital voltmeter calibrated to display gas concentration levels from either the combustible output signal, the oxygen output signal, or the output signal from the air displacement means.

5. A gas monitoring apparatus according to claim 1, wherein said air displacement means includes an inverting circuit means which receives said oxygen output signal from said oxygen sensing means.

6. A gas monitoring apparatus according to claim 5, wherein said inverting circuit means includes an operational amplifier having an input terminal connected to said oxygen sensing means for receiving said oxygen output signal and an output terminal connectable to said indicator means.

7. A gas monitoring apparatus according to claim 1, wherein said sampling means further includes a pump means for obtaining a sample of an atmospheric gaseous mixture.

8. A gas monitoring apparatus according to claim 7, wherein said sampling means further includes a probe connected to said pump means through which samples of atmospheric gaseous mixtures are obtained.

* * * * *